US007556832B2

(12) United States Patent
Kracke

(10) Patent No.: US 7,556,832 B2
(45) Date of Patent: Jul. 7, 2009

(54) PROCESS AND FORMULA FOR TREATING IRRITABLE BOWEL SYNDROME

(76) Inventor: Donald R. Kracke, 883 N. Crown Dr., Lake Arrowhead, CA (US) 92352

( * ) Notice: Subject to any disclaimer, the term of this patent is extended or adjusted under 35 U.S.C. 154(b) by 64 days.

(21) Appl. No.: 11/745,288

(22) Filed: May 7, 2007

(65) Prior Publication Data

US 2007/0264314 A1 Nov. 15, 2007

Related U.S. Application Data

(60) Provisional application No. 60/746,841, filed on May 9, 2006.

(51) Int. Cl.
*A61K 36/00* (2006.01)

(52) U.S. Cl. ...................................... 424/769; 424/776

(58) Field of Classification Search ....................... None
See application file for complete search history.

(56) References Cited

U.S. PATENT DOCUMENTS

| | | | | |
|---|---|---|---|---|
| 4,950,140 | A * | 8/1990 | Pflaumer et al. | 424/439 |
| 6,133,318 | A * | 10/2000 | Hart | 514/574 |
| 6,352,738 | B1 * | 3/2002 | Carels | 426/632 |
| 6,632,461 | B1 | 10/2003 | Slimak | |
| 6,803,035 | B2 | 10/2004 | Greenblatt et al. | |
| 6,805,883 | B2 * | 10/2004 | Chevaux et al. | 424/725 |
| 2005/0100535 | A1 * | 5/2005 | Farmer et al. | 424/93.46 |

* cited by examiner

*Primary Examiner*—Christopher R. Tate
(74) *Attorney, Agent, or Firm*—Kelly Lowry & Kelley LLP

(57) ABSTRACT

A process for treating irritable bowel syndrome wherein sometime before a meal, a user ingests a pill or tablet that slows down the muscles of their lower intestine that serve to push waste out from the user's digestive tract. At the same time, the user takes a fiber pill with a quantity of water. About forty five minutes after taking the aforementioned pills, the user ingests one to nine ounces, preferably three ounces, of a pecan-derived health supplement.

18 Claims, No Drawings

PROCESS AND FORMULA FOR TREATING IRRITABLE BOWEL SYNDROME

BACKGROUND OF THE INVENTION

The present invention relates generally to a health supplement. More particularly, the present invention relates to a food supplement bar directed towards individuals with irritable bowel syndrome.

There is a great need for a health supplement that can be applied to a wide range of uses. Over the years, many types of health supplements or products have been used to aid a user in achieving health benefits. However, such health supplements or products are often made from synthetic or otherwise processed ingredients and require complicated procedures during formulation. Even some health supplements derived from natural ingredients, such as egg yolks, require that those eggs be obtained from special sources prior to preparation. For example, U.S. Pat. No. 6,803,035 discloses an anti-diarrheal and method for using the same. However, this method requires that the egg product specifically be obtained from a hyper-immunized avian. This requires additional cost and effort in order to ensure that the egg comes from a hyper-immunized avian and is suitable for use. In another example, U.S. Pat. No. 6,632,461 discloses the use of tropical root crops in effective intervention strategies for treating difficult and complex cases and chronic diseases. However, the resort to the use of tropical roots can be impractical, as well as expensive, for many people.

Over 50,000,000 people in the United States of America are afflicted with some degrees of irritable bowel syndrome (IBS) at any given time of any given year. IBS is a problem that affects mainly the bowel, which is also called the large intestine. The bowel is the part of the digestive system that makes and stores waste (i.e., stool or fecal matter). The word syndrome means a group of symptoms. IBS is a syndrome because it can cause several symptoms. For example, IBS causes cramping, bloating, gas, diarrhea, and constipation. IBS is not a disease but rather a functional disorder, which means that the bowel does not work as it should. With IBS, the nerves and muscles in the bowel are extra-sensitive. For example, the muscles may contract too much when you eat. These contractions can cause cramping and diarrhea during or shortly after a meal. Or the nerves can be overly sensitive to the stretching of the bowel (because of gas, for example). Cramping or pain can result. IBS afflicts the young and the old, both men and women. People can become afflicted with IBS in different ways. For some people, IBS can result from a parasitic infection. IBS has no cure, but people have done various things to relieve symptoms including, but not limited to dietary changes, medicine, and stress relief.

Some foods make IBS worse (e.g., fatty foods like french fries, milk products like cheese or ice cream, chocolate, alcohol, caffeine (found in coffee and some sodas), carbonated drinks like soda or the like) while some foods make IBS better (e.g., Fiber). Fiber reduces IBS symptoms, especially constipation, because fiber makes stool soft, bulky, and easier to pass. Fiber is found in bran, bread, cereal, beans, fruit, and vegetables. Medicine is also used to help with symptoms (e.g., laxatives to treat constipation, antispasmodics to slow contractions in the bowel (which helps with diarrhea and pain) or the like). While so-called miracle drugs, such as Xifaxin (Rifaximan), have been developed to combat IBS, not every person is able to obtain the drug (due to he or she lacking health insurance or the ability to afford the drug) nor is every person able to take the drug without enduring harmful or discomforting side-effects.

While methods of preparing ingredients for use as a health supplement, such as the ones described above, may provide a heath supplement for use in a variety of applications, such methods and the types of ingredients used can always be improved to simplify the process of making such supplements.

Accordingly, there is a need for a simplified method of making a pecan-derived health supplement. There is a further need for a pecan-derived health supplement where the pecans do not have to come from any special source. There is also a need for a food supplement bar to be consumed by individuals suffering from IBS to alleviate the symptoms of IBS. The present invention fulfills these needs and provides other related advantages.

SUMMARY OF THE INVENTION

The process of the present invention for treating irritable bowel syndrome comprises the steps of ingesting an antispasmodic compound at least one hour before a meal, ingesting a fiber compound with water simultaneously with the antispasmodic compound, and ingesting one to nine ounces of a pecan-derived food supplement about forty-five minutes after ingesting the antispasmodic and fiber compounds. The antispasmodic compound may comprise Dicyclomine or an herbal supplement. The quantity of pecan-derived food supplement may be reduced to one to eight ounces.

The pecan-derived food supplement may be made by mixing ingredients consisting of pecans, sweetener, cloves, nutmeg, cinnamon and egg white together into a batter. This batter is then baked to a user's desired consistency. The batter may be formed into nutrition bars, cookies and/or clusters prior to baking. The pecans may be toasted, roasted or raw and may be whole, sliced, chopped, diced or in pieces. Specifically, the ingredients should comprise approximately two cups of pecans, one-half cup of sweetener, one-quarter teaspoon ground cloves, one-quarter teaspoon nutmeg, two teaspoons cinnamon, and one egg white. The ingredients may be organic or non-organic.

Additional steps that will help treat irritable bowel syndrome include avoiding spicy foods or lactose products and reducing by approximately one-third the amount of food ordinarily consumed in meal.

Other features and advantages of the present invention will become apparent from the following more detailed description.

DETAILED DESCRIPTION OF THE PREFERRED EMBODIMENT

The present invention provides a process and formula for creating a health supplement suitable for use in a mammalian gastrointestinal tract. The present invention also provides a method of making a food supplement bar to be consumed by individuals suffering from irritable bowel syndrome.

An embodiment of the present invention resides in a process and formula for making a food supplement bar that is derived, at least in part, from pecans. A food supplement bar includes two cups of pecans (toasted, roasted or raw; whole nuts or diced nuts), one half cup of a sweetener (natural (e.g., sugar, honey or the like) or artificial (e.g., Splenda, Nutrasweet or the like)), one quarter teaspoon ground cloves, one quarter teaspoon nutmeg, two teaspoons cinnamon, and one egg white. The preceding ingredients can be organic or non-organic. The preceding ingredients are mixed together and formed into a batter that can then be baked into the form of one or more nutrition bars, cookies, and/or large pecan clusters. The quantity of bars/cookies made varies depending on the desired size and shape of the bars/cookies.

Irritable bowel syndrome or IBS affects about ten to twenty percent of the general population and is one of the most commonly diagnosed conditions by gastroenterologists. As discussed above, fiber is an excellent means of lessening the effects of irritable bowel syndrome. In addition, vitamin E (both alpha and gamma tocopherols) is the primary antioxidant used by the body and has been shown to improve intestinal and prostate health. Pecans are an excellent source of both fiber and vitamin E. One ounce of pecans contains approximately ten percent of the recommended daily allowance of fiber. One 3.3 ounce bar of the pecan-derived food supplement described above contains approximately 4.39 grams of dietary fiber, 0.59 milligrams of vitamin E (alpha tocopherol) and 10 milligrams of vitamin E (gamma tocopherol).

Pecans also provide benefits for other systems in the body. Pecans contain more antioxidants than any other nut. Over ninety percent of the fat in pecans is unsaturated. The protein structure is similar to meat and the pecan is nutrient and energy dense. Pecans have been shown to lower LDL cholesterol levels and contain over nineteen vitamins and minerals. Regarding the other ingredients in the pecan-derived food supplement, cinnamon has been used to treat nausea, flatulence and diarrhea. Many herbs, including ginger, licorice root, and peppermint oil may be included to increase the effects of the pecan-derived food supplement on IBS.

Ginger—improves digestion—an excellent herb to use for any type of digestive upset or difficulty. It is stimulating and warming.

Licorice root—good for sensitive stomachs, aids in the production of natural substances that coat and therefore protect the stomach.

Peppermint oil—has an antispasmodic effect that can provide significant relief for the abdominal pain, bloating, alternating periods of constipation and diarrhea, and general abdominal discomfort associated with IBS.

Slippery Elm—inner bark mixed with water creates a soothing fiber. The fiber has several beneficial effects on digestion: 1) it reduces bowel transit time; 2) it absorbs toxins from the bowel; 3) it increases fecal bulk and dilutes stool materials thereby reducing stool contact with the intestinal mucosa; and 4) it enhances beneficial bacteria in the gut and provides an excellent substrate for bacterial fermentation.

Fennel—stimulates digestion, eliminates flatulence, relieves stomach cramps.

Rooibos—has antispasmodic properties which help to relieve stomach and digestive problems.

The food supplement bar/cookies may be ingested by themselves or in combination with one or more other products meant to relieve the symptoms of IBS. For example, one process of treating IBS in a subject in need of treatment includes orally administering a pill or tablet containing an antispasmodic substance (e.g., a twenty milligram tablet of Dicyclomine (Bentyl) or an herbal supplement) to the subject in order to slow down the muscles of the subject's lower intestine which serve to push waste (e.g., stool or fecal matter) out from the subject's digestive tract. This antispasmodic is administered one and a half hours before each meal. At the same time, a large capsule of a fiber pill (e.g., Metamucil or the like) can be orally administered with water. About forty five minutes after administering the intestine muscle slowing product and/or fiber pill, one to nine ounces, preferably three ounces, of the pecan-derived bar/cookies described above. are administered to the subject. The subject can supplement this by avoiding overly spiced foods and/or lactose products. Additionally, the subject can reduce by one third the amount of food consumed prior to taking the food bar/cookies. A subject can adjust the amount of pecans and the times between doses to suit their individual needs.

Other features and advantages of the present invention will become apparent from a review of the following articles and information sources:

From the web-site About IBS (www.aboutibs.org), article entitled About Irritable Bowel Syndrome (IBS), copyright 1999-2006 International Foundation for Functional Gastrointestinal Disorders, Inc., last updated Dec. 22, 2005.

From the Texas Pecan Growers Association (www.tpga.org/nutritionupdates.html), article entitled Nutrition/Health Updates, copyright 2002 Texas Pecan Growers Association.

California Pecan Growers Association (www.californiapecangrowers.org/pecannutrients.htm), article entitled About California Pecans, copyright 2004 California Pecan Growers Association.

Article from Beth Hubrich, M. S., R. D. (www.ilovepecans.org/pr_072602.html), article entitled Study Demonstrates Pecans A Consistent, Rich Source of the Beneficial Antioxidant Vitamin E, dated Jul. 26, 2002.

Article entitled Pecan Health Studies (http://aggiehorticulture.tamu.edu/plantanswers/recipes/pecanrecipes/healthstudies.html).

Chart of Dietary Reference Intakes (DRIs): Recommended Intakes for Individuals, Vitamins, Food and Nutrition Board, Institute of Medicine, National Academies, copyright 2004, The National Academy of Sciences.

Chart of Dietary Reference Intakes (DRIs): Recommended Intakes for Individuals, Elements, Food and Nutrition Board, Institute of Medicine, National Academies, copyright 2004, The National Academy of Sciences.

Chart of Dietary Reference Intakes (DRIs): Tolerable Upper Intake Levels (UL), Vitamins, Food and Nutrition Board, Institute of Medicine, National Academies, copyright 2004, The National Academy of Sciences.

Chart of Dietary Reference Intakes (DRIs): Tolerable Upper Intake Levels (UL), Elements, Food and Nutrition Board, Institute of Medicine, National Academies, copyright 2004, The National Academy of Sciences.

Charts entitled Dietary Reference Intakes (DRIs): Estimated Energy Requirements (EER) for Men and Women 30 Years of Age and Dietary Reference Intakes (DRIs): Acceptable Macronutrient Distribution Ranges, Food and Nutrition Board, Institute of Medicine, National Academies, from Dietary Reference Intakes for Energy, Carbohydrate, Fiber, Fat, Fatty Acids, Cholesterol, Protein, and Amino Acids, 2002.

Charts entitled Dietary Reference Intakes (DRIs): Recommended Intakes For Individuals, Macronutrients and Dietary Reference Intakes (DRIs): Additional Macronutrient Recommendations, Food and Nutrition Board, Institute of Medicine, National Academies, from Dietary Reference Intakes for Energy, Carbohydrate, Fiber, Fat, Fatty Acids, Cholesterol, Protein, and Amino Acids, 2002.

Chart entitled Dietary Reference Intakes (DRIs): Estimated Average Requirements for Groups, Food and Nutrition Board, Institute of Medicine, National Academies, from the National Academy of Sciences (2002).

Article from Wikipedia, Tocopherol (http://en.wikipedia.org/wiki/vitamin_e).

Compilation of materials presented in article entitled Vitamin E (Tocopherols and Tocotrienols) from Ben Best (www.benbest.com/nutrceut/VitaminE.html).

Article from Wikipedia, Oleic Acid (http://en.wikipedia.org/wiki/oleic_acid).

Article from Wikipedia, Linoleic Acid (http://en.wikipedia.org/wiki/linoleic_acid).

Article from Lipomics, 9,12-Octadecadienoic acid (Linoleic acid) (www.lipomics.com/resources/fatty_acids/18_2n6.htm).

Article from Kimberly Lummus, M. S., R. D. (www.ilovepecans.org/pecans_powerfood.html), article entitled Pecans Are Power Food, dated April, 2005.

Article entitled NUTrition Information (http://www.ilovepecans.org/nutrition.html), National Pecan Sheller's Association (2002).

Pecan info from http://www.vegparadise.com/highestperch65.html#Nutrition.

Article from Encyclopedia of Spices, Cinnamon, The Epicentre (www.theepicentre.com/Spices/cinnamon.html) (2003).

Medicinal Spices Exhibit—UCLA Biomedical Library: History & Special Collections, article on Cinnamon (http://unitproj.library.ucla.edu/biomed/spice/index.cfm?displayID=5), Regents of the University of California (2002).

Article on California Walnuts Health & Nutrition (www.walnuts.org/health/han_nutrients.asp), USDA Nutrient Database for Standard Reference, Release 15, August 2002. Excerpt from article entitled Almond Composition (www.almondsarein.com/health/almond_composition/.

Although an embodiment has been described in detail for purposes of illustration, various modifications may be made without departing from the scope and spirit of the invention. Accordingly, the invention is not to be limited, except as by the appended claims.

What is claimed is:

1. A process for treating irritable bowel syndrome in a subject in need thereof, comprising the steps of orally administering to the subject an antispasmodic compound at least one hour before a meal;

orally administering to the subject a fiber compound with water simultaneously with the antispasmodic compound; and orally administering to the subject one to nine ounces of a baked batter consisting of pecans, sweetener, cloves, nutmeg, cinnamon and egg white about forty-five minutes after administering the antispasmodic and fiber compounds.

2. The process of claim 1 wherein the antispasmodic compound comprises dicyclomine or an herbal supplement.

3. The process of claim 1 wherein the quantity of baked batter comprises one to eight ounces.

4. The process of claim 1 further comprising the step of forming the baked batter into nutrition bars, cookies and/or clusters.

5. The process of claim 1 wherein the pecans are toasted, roasted or raw.

6. The process of claim 1 wherein the pecans are whole, sliced, chopped, diced or pieces.

7. The process of claim 1 wherein the baked batter comprises two cups of pecans, one-half cup of sweetener, one quarter teaspoon ground cloves, one quarter teaspoon nutmeg, two teaspoons cinnamon, and one egg white.

8. The process of claim 1 wherein the baked batter is organic or non-organic.

9. The process of claim 1 further comprising the step of said subject avoiding spicy foods or lactose products.

10. The process of claim 1 further comprising the step of said subject reducing by approximately one-third the amount of food ordinarily consumed in a meal.

11. A process for treating irritable bowel syndrome in a subject in need thereof, comprising the steps of:

orally administering to the subject an antispasmodic compound at least one hour before a meal wherein the antispasmodic compound comprises dicyclomine or an herbal supplement;

orally administering to the subject a fiber compound with water simultaneously with the antispasmodic compound;

orally administering to the subject one to eight ounces of a baked batter consisting of pecans, sweetener, cloves, nutmeg, cinnamon and eggwhite about forty-five minutes after administering the antispasmodic and fiber compounds.

12. The process of claim 11 further comprising the step of forming the baked batter into nutrition bars, cookies and/or clusters.

13. The process of claim 11 wherein the pecans are toasted, roasted or raw.

14. The process of claim 11 wherein the pecans are whole, sliced, chopped, diced or pieces.

15. The process of claim 11 wherein the baked batter comprises two cups of pecans, one-half cup of sweetener, one quarter teaspoon ground cloves, one quarter teaspoon nutmeg, two teaspoons cinnamon, and one egg white.

16. The process of claim 11 wherein the baked batter is organic or non-organic.

17. The process of claim 11 further comprising the step of said subject avoiding spicy foods or lactose products.

18. The process of claim 11 further comprising the step of said subject reducing by approximately one-third the amount of food ordinarily consumed in a meal.

* * * * *

UNITED STATES PATENT AND TRADEMARK OFFICE

CERTIFICATE OF CORRECTION

PATENT NO. : 7,556,832 B2
APPLICATION NO. : 11/745288
DATED : July 7, 2009
INVENTOR(S) : Donald R. Kracke It is certified that error appears in the above-identified patent and that said Letters Patent is hereby corrected as shown below:

In column 6, line 29 (claim 11), after "pound;" insert -- and --.

Signed and Sealed this
Fourth Day of October, 2011

David J. Kappos
*Director of the United States Patent and Trademark Office*